United States Patent [19]

Awata et al.

[11] Patent Number: 4,602,026
[45] Date of Patent: Jul. 22, 1986

[54] OPHTHALMIC TOPICAL AGENT FOR REMEDY OF DISEASES OF IRIS AND CILIARY BODY

[75] Inventors: Takashi Awata, Amagasaki; Tomio Maenaka, Sanda; Yutaka Kawamatsu, Kyoto, all of Japan

[73] Assignee: Senju Pharmaceutical Co., Ltd., Osaka, Japan

[21] Appl. No.: 762,747

[22] Filed: Jul. 30, 1985

[30] Foreign Application Priority Data

Aug. 3, 1984 [JP] Japan .................................. 59-163923

[51] Int. Cl.$^4$ ............................................ A61K 31/425
[52] U.S. Cl. ...................................... 514/369; 514/912
[58] Field of Search ................. 514/369, 912; 548/183

[56] References Cited

U.S. PATENT DOCUMENTS 4,287,200  9/1981  Kawamatsu et al. ................ 548/183
4,387,101  6/1983  Kawamatsu et al. ................ 548/183

FOREIGN PATENT DOCUMENTS 33617  8/1981  European Pat. Off. ............ 514/369
28073  2/1982  Japan .................................... 548/183

Primary Examiner—Douglas W. Robinson
Attorney, Agent, or Firm—Berman, Aisenberg & Platt

[57] ABSTRACT

An ophthalmic topical agent for remedy of diseases of iris and ciliary body containing 5-(3-ethoxy-4-pentyloxyphenyl)-2,4-thiazolidinedione or its physiologically acceptable salt as an active ingredient.

15 Claims, No Drawings

OPHTHALMIC TOPICAL AGENT FOR REMEDY OF DISEASES OF IRIS AND CILIARY BODY

BACKGROUND OF THE INVENTION

1. Field of the Invention

This invention relates to an ophthalmic topical agent having a remedy action for diseases of iris and ciliary body and can be utilized in the medical field.

2. Description of the Prior Art

Iris diseases and ciliary body diseases are caused by diabetes, arthritis, gonorrhea, syphilis, tuberculosis, trauma and so forth. Example of these diseases includes iritis, iris paralysis, cyclitis, iridocyclitis, etc. and particularly, serious cases of them lead to loss of eyesight. In order to remedy these ophthalmic diseases, a causal treatment of curing the illness as their cause or a symptomatic treatment of administering atropine to the local area is adopted. Some relatively mild cases are cured by a causal treatment, but chronic serious cases cannot be cured even if the causative illness is cured radically by a causal treatment. Hence, hitherto there have been never known any curative measures for such serious diseases.

This invention has for an object to provide an ophthalmic topical agent for remedying diseases of iris and ciliary body.

SUMMARY OF THE INVENTION

The present invention resides in an ophthalmic topical agent for remedy of diseases of iris and ciliary body containing 5-(3-ethoxy-4-pentyloxyphenyl)-2,4-thiazolidinedione or a physiologically acceptable salt thereof as an active ingredient.

DETAILED DESCRIPTION OF THE INVENTION

In the ophthalmic topical agent of this invention, 5-(3-ethoxy-4-pentyloxyphenyl)-2,4-thiazolidinedion and its physiologically acceptable salt to be used as an active ingredient can be produced, for example, by a method disclosed in U.S. Pat. No. 4,387,101 [Japanese Published Unexamined Patent Application No. 57-28075 (1982)]. As the physiologically acceptable salt of 5-(3-ethoxy-4-pentyloxyphenyl)-2,4-thiazolidinedione, there may, for example, be an alkali-metal salt, such as sodium salt or potassium salt; alkaline-earth metal salt, such as calcium salt, etc. The ophthalmic topical agent of this invention can be obtained by pharmaceutical preparation of 5-(3-ethoxy-4-pentyloxyphenyl)-2,4-thiazolidinedione or its physiologically acceptable salt (hereinafter referred to as "active ingredient") according to a conventional formula.

Embodiment of the ophthalmic topical agent consists in, for example, a collyrium or an ophthalmic salve. The collyrium is in the form of a dispersion or a solution of the active ingredient in water, in which a buffer, dissolution-assisting agent, isotonicity-imparting agent, and if required, additional antiseptic and thickening agent are incorporated.

As the buffer there may be mentioned, for example, phosphates, boric acid, borax, organic acids, e.g. acetic acid, citric acid, amino acids, the dissolution-assisting agent includes, for example, nonionic surfactants e.g., polyoxyethylene sorbitan monooleate, polyoxyethylene stearyl triglyceride, polyethylene glycol, $\alpha$- or $\beta$-cyclodextrine and its derivative, etc. Example of the isotonicity-imparting agent includes boric acid, saccharose (e.g. mannitol), salts (e.g., sodium chloride), glycerine, etc. The antiseptic includes, for example, benzalkonium chloride, cetylpiperidinium chloride, chlorobutanol, methylparaben, propylparaben. The thickening agent includes, e.g., polyvinylpyrrolidone, methyl cellulose, hydroxypropylmethyl cellulose, hydroxyethyl cellulose, etc.

The active ingredient is added in a proportion of 0.001–5%, preferably 0.05–0.5% to the collyrium. The other additive ingredients are used each in a conventional proportion according to general formula of a collyrium. The buffer is added usually in an amount of 0.5–2%; the dissolution-assisting agent 0.05–5% for nonionic surfactants and 1–20% for cyclodextrine or its derivative; the isotonicity-imparting agent not more than 5%; the antiseptic 0.001–5%; and the thickening agent 0.05–5%.

The ophthalmic salve is a dispersion of the active ingredient in an ophthalmic salve base, to which dispersion a nonionic surfactant and, if required, an antiseptic are added. The nonionic surfactant includes, for example, polyoxyethylene sorbitan monooleate, polyoxyethylene stearyl triglyceride, polyethylene glycol, etc., and the antiseptic includes, for example, methylparaben or propylparaben. The active ingredient is added in an amount of 0.001–5%, preferably 0.05–0.5% to the ophthalmic salve. The other additives are used each in a similar amount to general formula of an ophthalmic salve. That is, the nonion surfactant is added in 0.05–5% and the antiseptic 0.001–0.2%.

The ophthalmic topical agent of this invention is used usually according to the foregoing formulae, but it may further contain an ingredient having another medicinal efficacy in addition to the active ingredient. If required, it may contain a further additive. For instance, it, optionally, additionally contains atropine and can thus be administered to patients with serious iritis, whereby the iritis can be remedied while applying the symptomatic treatment.

The ophthalmic topical agent of this invention can be prepared in usual manner with respect to the order, means and conditions of mixing of the respective ingredients.

The ophthalmic topical agent pertaining to this invention has a curing action to iris diseases and ciliary body diseases of mammals, e.g., rat, mouse, dog, cat, horse, monkey, human being, etc. and is useful for the remedy of these diseases. The iris diseases may include, e.g. iritis, iris paralysis, and the ciliary body diseases may include, e.g., cyclitis. The ophthalmic topical agent of this invention can also be applied to the remedy of iridocyclitis which is a deuteropathy of both diseases.

Administration can be done by instilling the ophthalmic topical agent as a collyrium or applying it as an eyesalve. Administration dose varies depending on the disease conditions, but is usually 0.001–0.4 mg/kg/day, preferably 0.01–0.08 mg/kg/day. For example, for adult human being, the dosage is 0.05–20 mg per day, preferably 0.5–4 mg per day. The daily dose can be administered in the form of divided portions of generally 1–8 times per day, preferably 3–5 times per day.

By the use of the ophthalmic topical agent of this invention it became possible to cure radically such iris diseases and ciliary body diseases that could have never been cured.

EXAMPLE 1

(Collyrium)

Tween 80, 0.05 g, and PEG 4000, 0.3 g, were dissolved completely in about 40 ml of purified water, and 1 ml of 8 N sodium hydroxide was added. To this was added 0.5 g of 5-(3-ethoxy-4-pentyloxyphenyl)-2,4-thiazolidinedion to dissolve it completely. Further, 0.9 g of boric acid was added. The resulting solution was adjusted to a pH of 6 by gradually adding dropwise 8 N hydrochloric acid with stirring. Thereafter, 7 ml of 0.1 % benzalkonium chloride was added and then, purified water was added to make the total volume 100 ml.

EXAMPLE 2

(Collyrium)

α-Cyclodextrin, 14 g, was dissolved in about 80 ml of purified water, and 0.1 g of 5-(3-ethoxy-4-pentyloxyphenyl)-2,4-thiazolidinedion was added and dissolved with stirring. To the solution were added 0.3 g of chlorobutanol, 4.8 g of mannitol and 0.2 g of acetic acid to dissolve them. The solution was adjusted to a pH of 6 by adding 1 N sodium hydroxide, and purified water was added to make the total volume 100 ml.

EXAMPLE 3

(Ophthalmic salve)

5-(3-Ethoxy-4-pentyloxyphenyl)-2,4-thiazolidinedion, 0.5 g, was placed in a mortar, and to this was added 2 g of fluid paraffin to grind and mix them well with a pestle. Further, 97.5 g of vaseline was added gradually to mix them.

EXPERIMENTAL EXAMPLE 1

Wister rats weighing about 100 g were divided into three groups each comprised of five. The first group and the second group were ingested with powder feedstuff containing 50% of galactose. During that period, the first group was instilled with the collyrium obtained in Example 1 and the second group was instilled with the base of the collyrium in Example 1 in both eyes four times a day. The third group was ingested with usual solid feedstuff and was not instilled in the eyes. Seven days after, the rats were anesthetized by pentobarbital and each epidermis of the central cornea was peeled off in a radius of 2 mm with iodoglass. Forty eight hours after the operation, the rats were killed and their specimens of eyeball tissue were prepared and observed under microscope. As a result, with the rats of second group there were observed a tendency of falling and degeneration of iris epidermis cells and adhesion of them to crystalline lens. In contrast, with the rats of first group instilled with the collyrium of this invention, a slight degeneration of the iris epidermis cells was observed and there was seen no adhesion of them to the crystalline lens.

EXPERIMENTAL EXAMPLE 2

Five male white rabbits weighing 2 kg were used. Each rabbit was instilled with the collyrium in Example 1 in the right eye and with a physiological sodium chloride solution in the left eye at a dose of one drop at 1 hour intervals eight times a day for 14 days. On the beginning day (the first day), 3rd day, 7th day, 10th day and 14th day of the instillation, conditions of the cornea, conjunctiva, iris and nictitating membrane of them were observed with unaided eyes. Further, the cornea surface dyed with fluorescein was observed with the aid of a slit-lamp microscope. As a result, a slight degree of rubefaction was found in some rabbits in their corneas, conjunctivae, irises and nictitating membranes, but the degree was not different between the right eye in which the collyrium of this invention was instilled and the left eye in which physiological sodium chloride solution was instilled. With the cornea surface dyed with fluorescein, no difference was seen between the right eye and the left eye, either. Consequently, it is deemed that the collyrium of this invention causes no lesion to the eye tissue.

EXPERIMENTAL EXAMPLE 3

Acute toxicity test was conducted on rats aged four weeks to which 5-(3-ethoxy-4-pentyloxyphenyl)-2,4-thiazolidinedione was administered. The results obtained are shown as follows.

(1) $LD_{50}$ Value

| Animal Kind | Administration Method | $LD_{50}$ Value (mg/kg) Male | Female |
| --- | --- | --- | --- |
| Mouse | Intraperitoneal injection | 560 | 500 |
|  | Subcutaneous injection | 1720 | 2270 |
|  | Oral administration | 2320 | 2150 |
| Rat | Intraperitoneal injection | 490 | 520 |
|  | Subcutaneous injection | 3210 | 3300 |
|  | Oral administration | 5300 | 4330 |

(2) General Symptoms

The following symptoms in common with the mice and rats were observed.

Intraperitoneal injection group: From a few minutes on after the administration, suppression of spontaneous motility and walking disorder were seen depending on the dose. Thereafter, they were sedate in prone state and there were observed decrease of response to external stimulus, lowering in tonus of the systemic muscle, disappearance of righting reflex, lacrimation and respiratory depression. With the mice, in addition to the above, projection of the eyeball, a secretion in the margin of palpebra, fall of the body surface temperature and a slight degree of tremor in a few cases were seen.

Subcutaneous injection group: At high and medium doses, 3 or 5 hours after the administration, a slight suppression of spontaneous motility was found, and then, lowering in tonus of the abdominal muscle, walking disorder, lacrimation and respiratory depression were observed. With the mice, on the next day after the administration, projection of the eyeball, a secretion in the margin of palpebra and fall of the body surface temperature were additionally seen.

Oral administration group: From one hour after the administration, spontaneous motility began to suppress depending on the dosage and then, walking disorder, decrease of response to external stimulus, lowering in tonus of the systemic muscle, disappearance of righting reflex and a slight degree of tremor in a few cases occurred with time. With the mice, lacrimation, a secretion in the margin of palpebra and fall of the body surface temperature were additionally observed. The life periods in the death cases of both animals were, upon intraperitoneal administration, 2–24 hours, upon subcutaneous administration, from the night of the administration day to three days after the administration; and, upon oral administration, 2–24 hours in major cases or 2–4 days in minor cases.

(3) Observation on Dissection

In the death cases, congestion of the lung was observed in both mice and rats. In the survival cases, the rats of subcutaneous administration group were formed with a cyst of hen's egg size in the injection area, and the cyst was found to contain an extremely small amount of unabsorbed medicament and a small amount of extravasation liquid. In the case of some of the rats of oral administration group, atrophy of the thymus gland was further seen.

REFERENCE EXAMPLE 1

24.6 g of α-chloro-α-(3-ethoxy-4-pentyloxyphenyl) acetonitrile and 10.2 g of thiourea in 100 ml of ethylene glycol monomethyl ether are stirred at 90–100° C. for 10 minutes. After addition of 150 ml of 2N-HCl at 110° C., the mixture is further stirred for 15 hours. After cooling, water is added and extraction is carried out with ethyl acetate. The extract is washed with water, dried (MgSO$_4$) and distilled to remove the solvent. The above procedure gives 16 g (56.2%) of 5-(3-ethoxy-4-pentyloxyphenyl)-thiazolidine-2,4-dione. Recrystallization from dilute ethanol gives colorless platelets, m.p. 104.5° C.–106° C.

REFERENCE EXAMPLE 2

In 4 ml of 2-methoxyethanol is dissolved 2 g of α-(3-ethoxy-4-pentyloxyphenyl)-α-hydroxyacetonitrile. To the solution, 866 mg of thiourea and 2.75 ml of concentrated hydrochloric acid are added. The mixture is stirred at 57° C.–65° C. for 2 hours. After adding 1 ml of water the mixture is refluxed for 5 hours. To the reaction mixture are added 15 ml of hexane-ethyl acetate (25:3) and 15 ml of water. The resulting crystals are collected by filtration, whereby 2.1 g of 5-(3-ethoxy-4-pentyloxyphenyl)thiazolidine-2,4-dione are obtained as scale-like colorless crystals.

REFERENCE EXAMPLE 3

In 7.5 ml of 2-methoxyethanol is dissolved 2.36 g of 3-ethoxy-4-pentyloxybenzaldehyde. While the solution is stirred at a temperature not exceeding 25° C., 0.83 ml of concentrated hydrochloric acid and solution of 0.56 g sodium cyanide in 1.5 ml of water are added in that order. After the solution is stirred for one hour, 1.14 g of thiourea and 3.6 ml of concentrated hydrochloric acid are added to the solution. The solution is stirred at 60° C.–65° C. for 2.5 hours and refluxed for 4 hours. After cooling the reaction mixture, 22 ml of hexane-ethyl acetate (25:3) and 15 ml of water is added. The mixture is stirred for 0.5 hour to give crystals. The crystals are collected by filtration and dried. The procedure gives 2.2 g of 5-(3-ethoxy-4-pentyloxyphenyl)-thiazolidine-2,4-dione as scale-like colorless crystals. Recrystallization from diluted ethanol gives crystals melting at 104° C.–105° C.

REFERENCE EXAMPLE 4

In 50 ml of 2-methoxyethanol is dissolved 23.6 g of 3-ethoxy-4-pentyloxybenzaldehyde. While the solution is stirred at 20° C., 6.9 g of acetic acid and a solution of 5.64 g sodium cyanide in 10 ml of water are added in that order. After the solution is stirred for 0.5 hour, 11.4 g of thiourea and 36 ml of concentrated hydrochloric acid are added to the solution. The solution is stirred at 57° C.–64° C. for 2 hours and refluxed for 4 hours. After cooling the reaction mixture, 224 ml of hexane-ethyl acetate (25:3) and 150 ml of water are added. The mixture is stirred on a ice-bath for 0.5 hour. The resulting crystals are collected by filtration and dried. The procedure gives 25.0 g of 5-(3-ethoxy-4-pentyloxyphenyl)-thiazolidine-2,4-dione as scale-like colorless crystals. Recrystallization from diluted ethanol gives crystals melting at 104° C.–105° C.

What is claimed is:

1. A method for treating iritis, iris paralysis, cyclitis or iridocyclitis which comprises topically administering an effective amount of 5-(3-ethoxy-4-pentyloxyphenyl)-2,4-thiazolidinedione or a pharmaceutically-acceptable salt thereof to an infected eye afflicted with one of these conditions.

2. A method as claimed in claim 1 wherein the 5-(3-ethoxy-4-pentyloxyphenyl)-2,4-thiazolidinedione or pharmaceutically-acceptable salt thereof is active ingredient and is in collyrium form.

3. A method as claimed in claim 2 wherein the active ingredient comprises from 0.001 to 5 percent of the collyrium.

4. A method as claimed in claim 1 wherein the 5-(3-ethoxy-4-pentyloxyphenyl)-2,4-thiazolidinedione or pharmaceutically-acceptable salt thereof is active ingredient and is in ophthalmic salve form.

5. A method as claimed in claim 4 wherein the active ingredient comprises from 0.001 to 5 percent of the ophthalmic salve.

6. A method as claimed in claim 2 for treating iritis.

7. A method as claimed in claim 2 for treating iris paralysis.

8. A method as claimed in claim 2 for treating cyclitis.

9. A method as claimed in claim 2 for treating iridocyclitis.

10. A method as claimed in claim 4 for treating iritis.

11. A method as claimed in claim 4 for treating iris paralysis.

12. A method as claimed in claim 4 for treating cyclitis.

13. A method as claimed in claim 4 for treating iridocyclitis.

14. A physiologically-acceptable ophthalmic topical salve composition useful for treating iritis, iris paralysis, cyclitis and iridocyclitis and comprising a suitable salve carrier and an effective amount of 5-(3-ethoxy-4-pentyloxyphenyl)-2,4-thiazolidinedione or of a physiologically-acceptable salt thereof as an active ingredient.

15. An ophthalmic topical composition as claimed in claim 14 wherein said active ingredient is incorporated in an amount of from 0.001–5%.

* * * * *